United States Patent [19]

Smith et al.

[11] Patent Number: 4,544,792
[45] Date of Patent: Oct. 1, 1985

[54] UPGRADING FISCHER-TROPSCH OLEFINS

[75] Inventors: Fritz A. Smith, New Hope, Pa.; Samuel A. Tabak, Wenonah, N.J.

[73] Assignee: Mobil Oil Corporation, New York, N.Y.

[21] Appl. No.: 681,413

[22] Filed: Dec. 13, 1984

[51] Int. Cl.$^4$ .......................... C07C 1/20; C07C 3/06
[52] U.S. Cl. .................................... 585/533; 502/53; 585/310; 585/322; 585/327; 585/415; 585/520; 585/639; 585/733
[58] Field of Search ............... 585/415, 533, 520, 639, 585/733, 310, 322, 326, 327; 502/53

[56] References Cited

U.S. PATENT DOCUMENTS

| | | | |
|---|---|---|---|
| 3,760,024 | 9/1973 | Cattanach | 585/415 |
| 3,960,978 | 6/1976 | Givens et al. | 585/533 |
| 4,052,477 | 10/1977 | Ireland et al. | 585/469 |
| 4,111,792 | 9/1978 | Caesar et al. | 208/79 |
| 4,126,644 | 9/1978 | Caesar et al. | 208/950 |
| 4,227,992 | 10/1980 | Garwood et al. | 208/46 |
| 4,279,830 | 7/1981 | Haag et al. | 585/415 |
| 4,324,940 | 4/1982 | Dessau | 585/466 |
| 4,358,395 | 11/1982 | Haag et al. | 585/640 |
| 4,423,272 | 12/1983 | Forbus et al. | 585/640 |
| 4,433,185 | 2/1984 | Tabak | 585/415 |
| 4,456,781 | 6/1984 | Marsh et al. | 585/533 |
| 4,465,884 | 8/1984 | Degnan et al. | 585/415 |
| 4,517,396 | 5/1985 | Hoek et al. | 585/415 |

OTHER PUBLICATIONS

M. E. Dry, "High Yield High Quality Diesel from Fischer-Tropsch Process, ChemSA Feb. 1984.

Primary Examiner—D. E. Gantz
Assistant Examiner—A. Pal
Attorney, Agent, or Firm—A. J. McKillop; M. G. Gilman; L. G. Wise

[57] ABSTRACT

A process for converting olefinic feedstock, such as synthol olefinic liquid product of Fischer-Tropsch synthesis, to distillate hydrocarbons comprising the steps of contacting the feedstock at elevated temperature and pressure with acid zeolite conversion catalyst to oligomerize olefins and convert oxygenated hydrocarbons contained in said light oil at temperatures up to 325° C. and in the presence of $H_2$, thereby providing an effluent containing heavy distillate range hydrocarbon, light gas and byproduct water.

13 Claims, 3 Drawing Figures

4,544,792

UPGRADING FISCHER-TROPSCH OLEFINS

FIELD OF INVENTION

This invention relates to a continuous process for the manufacture of distillate range hydrocarbon fuels. In particular it provides a system for operating an MOGD type plant wherein a oligomerization catalyst, such as crystalline zeolite of the ZSM-5 type, is employed for converting olefinic feedstocks containing alkenes and oxygenates at elevated temperature and pressure.

BACKGROUND OF THE INVENTION

Conversion of lower olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins, are converted into an olefinic gasoline blending stock by contacting the olefins with a catalyst bed made up of a ZSM-5 type zeolite. In a related manner, U.S. Pat. Nos. 4,150,062, 4,211,640 and 4,227,992 (Garwood et al) discloses processes for converting olefins to gasoline and/or distillate components. In U.S. Pat. No. 4,456,779 Owen et at disclose operating conditions for the Mobil Olefin to Gasoline/Distillate (MOGD) process for selective conversion of $C_3^+$ olefins to mainly aliphatic hydrocarbons. Typically, the process recycles gas or liquid hydrocarbons from a high-temperature, high-pressure separator downstream of the catalyst bed back into the reaction zone where additional olefins are converted to gasoline and distillate products. If the reaction of the olefins in converting them to distillate and gasoline is allowed. to progress in the catalyst stream without any measures taken to prevent the accumulation of heat, the reaction becomes so exothermically accelerated as to result in high temperatures and the production of undesired products.

In the process for catalytic conversion of olefins to heavier hydrocarbons by catalytic oligomerization using a medium pore shape selective acid crystalline zeolite, such as ZSM-5 type catalyst, process conditions can be varied to favor the formation of either gasoline or distillate range products. At moderate temperature and relatively high pressure, the conversion conditions favor aliphatic distillate range product having a normal boiling point of at least 165° C. (330° F.). Lower olefinic feedstocks containing $C_2$–$C_8$ alkenes may be converted; however, the distillate mode conditions do not convert a major fraction of ethylene. One source of olefinic feedstocks of interest for conversion to heavier fuel products is the intermediate olefin-rich naphtha or light oil obtained as a liquid product from Fischer-Tropch conversion of synthesis gas. A typical feedstock consists essentially of $C_3$–$C_6$ mono-olefins with a minor amount of coproduced oxygenate from Fischer-Tropsch synthesis. These feedstocks are suitable for upgrading to more valuable heavier hydrocarbon; however, the organic oxygenated content may cause catalyst aging due to formation of coke during the conversion process.

During the course of a single catalyst cycle, reactor temperatures must be raised to maintain the desired conversion of olefins to gasoline and/or distillate, and to maintain desired product liquid quality. Beyond a certain temperature, these objectives cannot be met and the catalyst must be regenerated. It is desirable to minimize the frequency of regenerations by decreasing the temperature aging rate. This reduces the inconvenience and cost of frequent regenerations, and may also extend the ultimate life of the catalyst, which experiences permanent activity loss over the course of many regenerations.

It is a main object of this invention to provide a continuous process devised for upgrading synthol intermediate olefins to a valuable heavy distillate fuel product.

SUMMARY OF THE INVENTION

A technique has been found for preventing or inhibiting coke deposition during the conversion. A continuous process is provided for converting a feedstock mixture comprising a major amount of lower olefins and a minor amount of oxygenated hydrocarbons to higher hydrocarbons comprising distillate product, including the step of contacting the feedstock in the presence of hydrogen with a shape selective medium pore acid zeolite oligomerization catalyst under reaction conditions at elevated temperatures in a pressurized reactor zone to convert olefins to heavier hydrocarbons. Preferably the conversion is followed by reducing pressure on effluent from the reactor zone to flash volatile components into a vapor phase and recover a heavy liquid stream from a phase separator, condensing a major portion of the vapor phase by cooling under pressure to recover a liquid intermediate olefin stream and recover condensed water by-product from oxygenate conversion to hydrocarbons, and fractionating the heavy liquid stream from the flashed reactor effluent to recover a heavy distillate hydrocarbon product stream. This technique is particularly useful in extending catalyst life by inhibiting coke formation on the catalyst due to oxygenate conversion.

A recycle stream containing olefinic boiling range components may be further converted into distillate product. In conjunction with reactor operating conditions, the recycle composition and rate determine the distillate product boiling range and properties such as viscosity.

These and other objects and features of the invention will be understood from the following detailed description and drawings.

THE DRAWINGS

DESCRIPTION OF THE PREFERRED EMBODIMENTS

Figure 1:
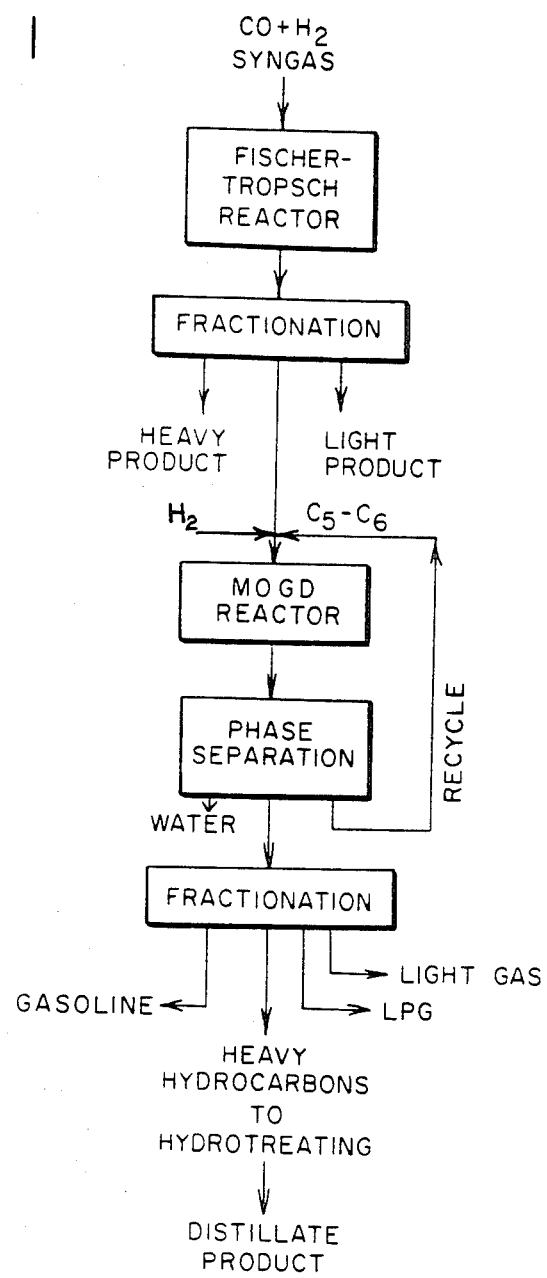
FIG. 1 is a process flow sheet showing the major unit operations and process streams.

The amount of cofed hydrogen sufficient to inhibit coke formation may vary considerably within the inventive concept. Feedstocks containing trace amounts of oxygenates can be mixed with a relatively small amount; e.g., as little as 1 mole % $H_2$. Increased oxygenate content will require a greater amount of hydrogen. It is preferred to operate the process with a minor amount of hydrogen, usually less than 50 mole %, in order to avoid diluting the olefinic feed components. It is known that pure olefins, such as propene, can be oligomerized over HZSM-5 without substantially modifying the reaction except for the partial pressure. The presence of hydrogenation components such as Ni, Pt, etc., can interfere with the desired process steps and should be avoided in the presence of hydrogen.

The oxygenate content of Fischer-Tropsch light oil can be controlled by pretreatment of the feedstock by extraction or the like. If the same oxygenate impurities are fed to the unit under steady state conditions, the water recovery rate can indicate the average oxygenate content, and this is an indirect measure of the potential for coke formation inherent in the feedstock. Thus, hydrogen feed rate can be regulated as a function of feedstock oxygenate content, usually with a preset minimum $H_2$ feed to assure adequate protection in the event of oxygenate surges. One skilled in the art of chemical process control will be able to modify the process flow streams to accomodate the changes in process conditions, as required.

The oligomerization catalysts preferred for use herein include the crystalline aluminosilicate zeolites having a silica to alumina ratio of at least 12, a constraint index of about 1 to 12 and acid cracking activity greater than 120, preferably about 160 to 200. Representative of the ZSM-5 type zeolites are ZSM-5, ZSM-11, ZSM-12, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable shape selective medium pore catalyst for fixed bed is HZSM-5 zeolite with alumina binder in the form of cylindrical extrudates of about 1-5 mm. Other pentasil catalysts which may be used in one or more reactor stages include a variety of medium pore ($\sim$5 to 9 Å) siliceous materials such as borosilicates, ferrosilicates, and/or aluminosilicates disclosed in U.S. Pat. Nos. 4,414,423, 4,417,086, 4,417,087 and 4,417,088, incorporated herein by reference.

The zeolite catalyzes a number of known reactions in addition to the oligomerization-interpolymerization reactions which are favored in producing the $C_{10}-C_{20}$ or higher molecular weight aliphatic materials useful as distillate fuel, etc. At higher temperatures, acid cracking tends to diminish product yield. Brönsted acid sites are provided by strong aluminosilicates and it is preferred to maintain a high effective $\alpha$-value, although certain metal cation-exchanged zeolites may be useful.

Catalyst aging can be caused by accumulation of very heavy product and/or process coke. It is known that relatively pure olefin feedstocks cause only minor deposition of non-strippable coke. The heavy hydrocarbonaceous deposits accumulated by non-oxygenated hydrocarbon can be stripped by high temperature gases. Harder process coke which results from dehydration and conversion reactions involving alcohols, ketones, aldehydes, etc., cannot be adequately rejuvenated or regenerated by stripping alone, and oxidative reactivation is required to restore the catalyst to substantially full activity.

The flowsheet diagram of FIG. 1 shows the relationship of the inventive process to the preceding syngas conversion and prefractionation unit operations, depicting the further conversion of the $C_5-C_6$ rich olefinic intermediate, phase separation and recycle. Heavy hydrocarbons are recovered by fractionation and sent to a conventional hydrotreating unit for product finishing.

Figure 2:
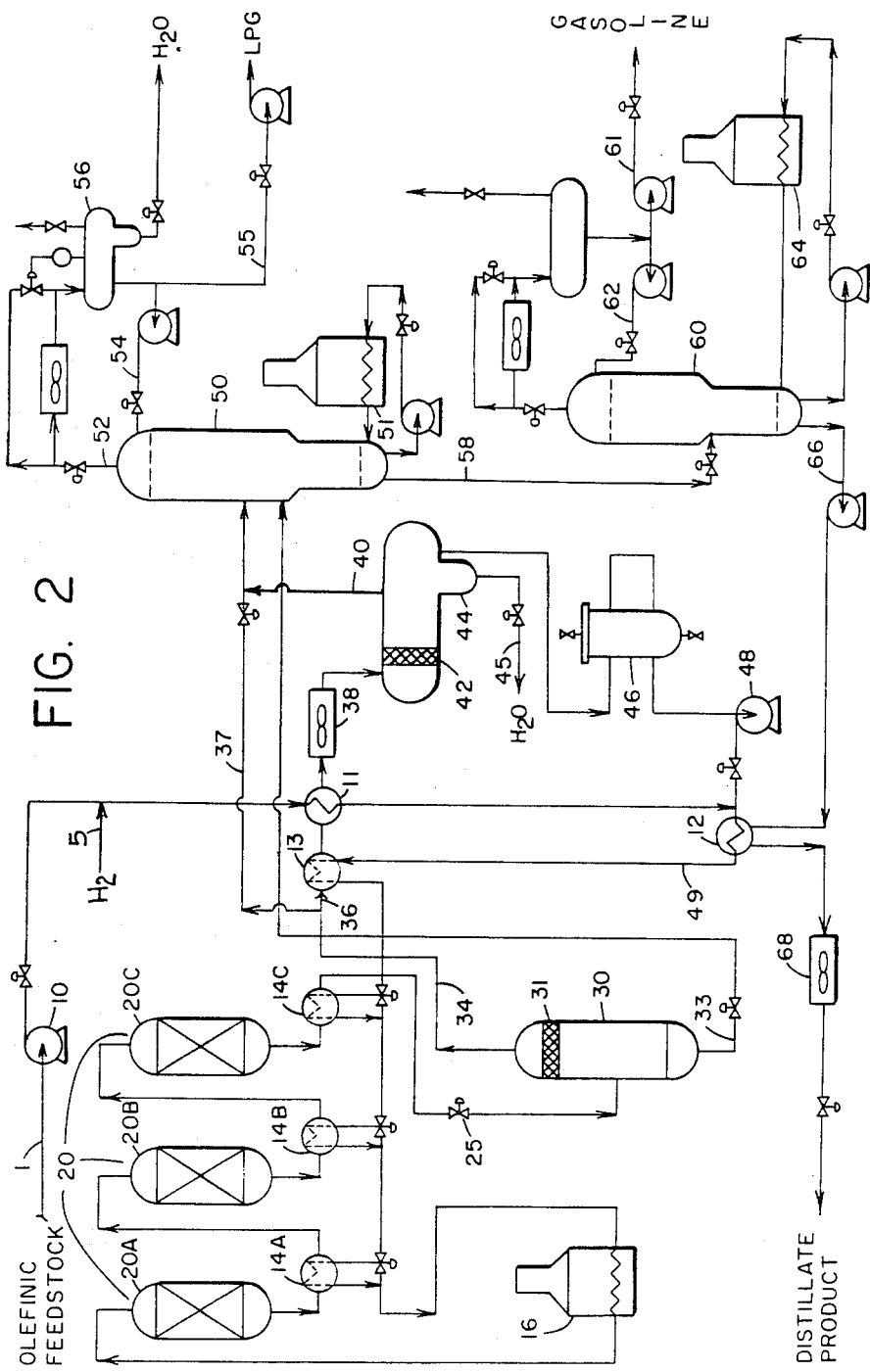
FIG. 2 is a schematic representation of a fixed bed reactor system and product separation system.

The present invention provides a continuous economic process for converting lower olefins to heavier hydrocarbons. It is an object of the present invention to separate olefinic gasoline from reactor effluent in an efficient manner to provide a recycle stream rich in $C_5$ to $C_9$ hydrocarbons and having only minor amounts of $C_4^-$ compounds or distillate range product. The gasoline recycle stream is obtained by a phase separation technique wherein the reactor effluent stream is cooled to condense heavy hydrocarbons, especially distillate materials, which are recovered in a liquid stream. These aspects are shown in greater detail in FIG. 2 and in the following description.

GENERAL PROCESS DESCRIPTION

The olefinic feedstock supply 1 is normally liquid and can be brought to process pressure by means of pump 10. Pressurized hydrogen gas is supplied via conduit 5 and combined with feedstock, which is preheated by passing sequentially through a series of heat exchange means 11, 12, 13 and reactant effluent exchangers 14C, B, A, and furnace 16 prior to entering the catalytic reactor system 20.

A typical distillate mode first stage reactor system 20 is shown. A multi-reactor system is employed with inter-zone cooling, whereby the reaction exotherm can be carefully controlled to prevent excessive temperature above the normal moderate range of about 230° to 325° (450°-620° F.). While process pressure may be maintained over a wide range, usually from about 2800 to over 10,000 kPa (400-1500 psia), the preferred pressure is about 4000 to 7000 kPa (600 to 1000 psia). The feedstock is heated to reaction temperature and carried sequentially through a series of zeolite beds 20A, B, C wherein at least a portion of the olefin content is converted to heavier distillate constituents. Advantageously, the maximum temperature differential across only one reactor is about 30° C. ($\Delta T \sim 50°$ F.) and the space velocity (LHSV based on olefin feed) is about 0.5 to 1.5. The heat exchangers 12A and 12B provide inter-reactor cooling and 12C reduces the effluent to flashing temperature. Control valve 25, operatively connected between the reactor section 20 and phase separator unit 30 provides means for reducing the process pressure, thereby vaporizing volatile components of the effluent stream, such as unreacted lighter hydrocarbons (e.g. $C_5-C_6$ alkenes) and water. The separator may be a vertical cylindrical vessel having a hooded tangential inlet to effect separation of the flashed effluent mixture. A demister pad 31 prevents substantial liquid entrainment and a major amount of the overhead vapor is withdrawn through conduits 34, 36, cooled indirectly by incoming feedstock in exchangers 13, 11 and passed through air cooler 38 to condense the lighter and intermediate range hydrocarbons in the separator vapor phase along with unreacted hydrogen and byproduct water from oxygenate conversion. Separator tank 42 has an overhead gas conduit 40 for removing a hydrogen-rich stream and separates a water phase, which is withdrawn from the system through boot 44 and outlet 45. Condensed hydrocarbons provide essentially all of the liquid olefinic recycle stream and is passed through filter means 46 and pressurized by pump means 48 prior to combining with feedstock in conduit 49.

It is understood that design modification can be made to provide for recovery and recycle of hydrogen. For instance, vapor stream 40 may be further cooled by a heat exchanger to condense at least a portion of the hydrocarbon for recovery in an additional phase separator (not shown). Recovered hydrogen-rich gas can be compressed, purified and recycled to the reactor system along with makeup hydrogen 5. Condensed liquids from the optional final separation unit can be fed via line 37 to debutanizer 50.

Liquid hydrocarbons rich in distillate are recovered from phase separator 30 at flashing pressure, preferrably about 1100 to 1500 kPa (160 to 220 psia) and passed via conduit 33 to debutanizer fractionation tower 50 at a lower stage therein where the heavy liquid contacts rising vapor from reboiler section 51 to vaporize dissolved lighter hydrocarbons, especially $C_4^-$ hydrocarbons present in the feedstock or generated during conversion. The debutanizer overhead stream 52 may be cooled to produce reflux 54 and recovered as LPG byproduct through conduit 55 from accumulator 56.

The amount of recycle can be varied according to need. During steady state operation at design conditions, a minor amount (e.g. 7-8%) of separator overhead vapor from line 34 may be taken as a slipstream through conduit 37 and sent directly to the debutanizer tower 50 at an intermediate stage. Light hydrocarbons and byproduct water are withdrawn with the tower overhead stream 52 and heavier hydrocarbons containing gasoline and/or distillate range hydrocarbons are sent along with the debutanizer bottoms stream 58 to product splitter 60 where the heavier hydrocarbons are fractionated to provide a condensed gasoline product 61 and condensed reflux 52. Light gas from separator 56 is rich in $H_2$ and $C_2^-$ components. This off gas may be used as fuel gas, or the hydrogen may be recovered by a hydrogen purification unit (not shown) and recycled under pressure, as described above.

Splitter tower 60 has a furnace fired reboiler section 64 and the refined heavy distillate product is recovered through conduit 66, and cooled by incoming feedstock in exchanger 12 and in cooler 68. Advantageously, the distillate-rich liquid phase is fractionated to provide a major product stream consisting essentially of 154° C.+ aliphatic hydrocarbons comprising a major amount of $C_{10}-C_{20}$ aliphatic hydrocarbons. This product may then be hydrotreated to provide a heavy distillate product.

There are several advantages to the process design. Usually the intermediate liquid recycle consists essentially of $C_5^+$ hydrocarbons, with minor amounts of $C_4^-$ components. This recycle material has a relatively high heat capacity and provides a good heat sink without diminishing feedstock olefin partial pressure and thereby maintaining a high olefin partial pressure at reactor inlet. The distillate product quality is readily altered by changing the average molecular weight of recycled olefins. By increasing temperature in the separator units, a heavier distillate product with regulated viscosity is obtained, and the recycled portion is further upgraded to heavier product by further reaction. The liquid recycle is economically repressurized by pumping, which requires modest power consumption. The debutanizer is operable at about 1000 kPa (150 psi) to condense all overhead without refrigeration, thus providing energy efficiency in obtaining the LPG byproduct. The product splitter tower can be operated at atmospheric pressure, thus holding the bottoms temperature to less than 273° C. (525° F.) to provide raw distillate product stability.

A typical distillate mode oligomerization operation is conducted over a fixed bed of HZSM-5/alumina extrudate catalyst using the techniques described in U.S. Pat. No. 4,456,779 (Owen et al) and U.S. Pat. No. 4,433,185, (Tabak), incorporated herein by reference. Reactor sequencing and catalyst regeneration are known in the art.

Feedstock may be derived from synthesis gas conversion product made according to a commercial Fischer-Tropsch process (SASOL), disclosed in U.S. Pat. No. 4,111,792. Typically, such materials have an oxygenated hyrocarbon content of about 0.5 to 10 wt percent. A $C_3-C_6$ (82.5 wt.%) olefin fractionation cut containing coproduced alcohol, ester, aldehyde, and/or ketone oxygenates is water washed to remove excess oxygenates and reduce their amount to less than 1 wt percent. The oligomerization feedstock properties for a preferred embodiment are set forth in Table I.

TABLE I

| FEED PROPERTIES | |
|---|---|
| Hydrocarbon Component | Weight Percent (wt %) |
| $C_2$ | 0.1 |
| Propene | 11.6 |
| Other $C_3$ | 2.1 |
| Butenes | 24.5 |
| Butanes | 4.0 |
| Pentenes | 7.1 |
| Pentanes | 4.7 |
| Hexenes | 19.3 |
| Hexanes | 3.8 |
| $C_7^+$ | 2.8 |
| Dienes, | nil |
| Sulfur | nil |
| Nitrogen | nil |
| Oxygenates, Wt % | 0.6 |
| CATALYST | |
| 65 wt % HZSM-5 (crystal size > 1 micron) | |
| 35 wt % $Al_2O_3$ | |
| $\alpha \sim 180$ | |

EXAMPLE 1

The above feedstock is upgraded by reaction over ZSM-5 zeolite under conditions sufficient to convert at least 95% of the butenes and, with recycle, to produce at least 70 wt.% distillate range product having an average viscosity of 3 centistokes. The process is run at 5600 kPa (800 psig) total pressure. The recycle is composed of $C_5$ to 450° F. hydrocarbons separated from the reactor effluent and returned to the reactor at a ratio of 2 parts recycle per part by volume of fresh feed. The average weight hourly space velocity is about 1, based on parts of fresh feed per part of catalyst. In one run the feedstock plus recycle is co-fed with hydrogen (about 6 mole%) and in the comparative example hydrogen is omitted and an inert diluent ($N_2$) added. The effect of hydrogen addition on distillate properties is shown in Table II.

TABLE II

| PRODUCT PROPERTIES | | |
|---|---|---|
| (ideal gas $P_{H_2}$ partial pressure, psia) | 0 | 50 |
| $P_{H_2}$ | 70 | 0 |
| $P_{Total}$ (psig) | 800 | 800 |
| 450° F. + Distillate Properties | | |
| Density, g/cc @ 60° F. | .8091 | .8044 |
| Viscosity, centistokes | 3.45 | 3.34 |
| Distillation, °F. | | |
| 10 wt % vaporized | 476° F. | 462° F. |
| 30 wt % vaporized | 502° F. | 493° F. |
| 50 wt % vaporized | 532° F. | 529° F. |
| 70 wt % vaporized | 574° F. | 576° F. |

TABLE II-continued

PRODUCT PROPERTIES

| | | |
|---|---|---|
| 90 wt % vaporized | 649° F. | 652° F. |

Figure 3:
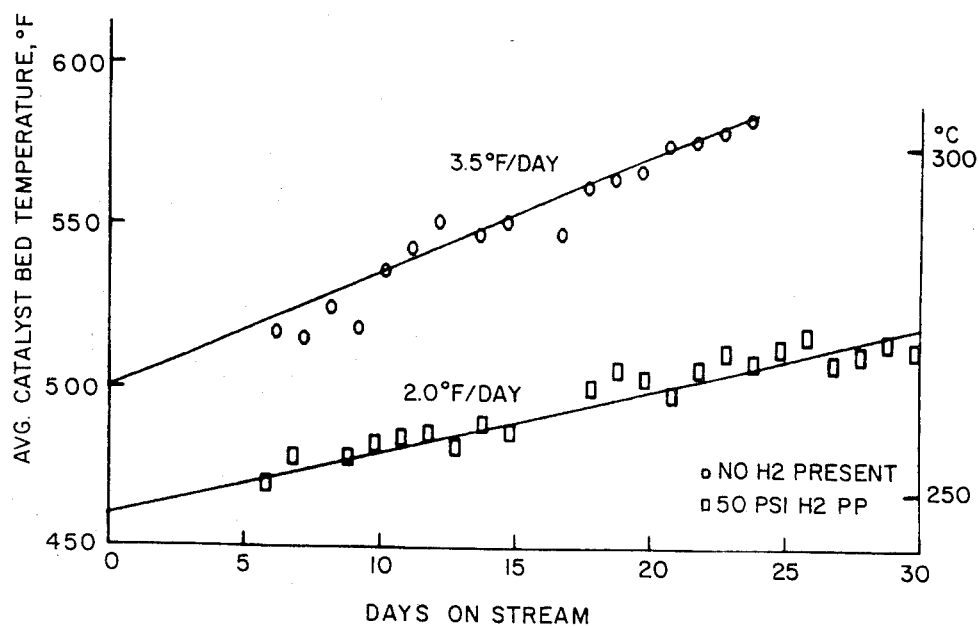
FIG. 3 is a graphic plot of reactor temperature vs stream time for comparative runs.

During each of the continuous runs, the catalyst bed temperature was increased to maintain conversion and product quality. The catalyst aging rate was reduced by about 40% by addition of $H_2$, as shown graphically in FIG. 3.

EXAMPLE 2

The procedure of Example 1 is repeated, except that the oxygenate content of the feedstock is about 2 wt%. Similar results are obtained in a 40-day continuous run, and the addition of hydrogen lowers the average aging rate to about 2.4° F./day.

Co-feeding hydrogen to the reactor reduces start of cycle temperature and reduces the amount of aging. The scope of this concept is not limited to aging caused solely by oxygenate compounds. Aging may be caused by other contaminants or due to more severe operating conditions.

Various modifications can be made to the system, especially in the choice of equipment and non-critical processing steps. While the invention has been described by specific examples, there is no intent to limit the inventive concept as set forth in the following claims.

What is claimed is:

1. A continuous process for converting a feedstock mixture comprising a major amount of lower olefins and a minor amount of oxygenated hydrocarbons to higher hydrocarbons including distillate product comprising:

contacting the feedstock in the presence of about 1 to 50 mole percent hydrogen with a shape selective medium pore oligomerization acid zeolite catalyst under reaction conditions at elevated temperature up to about 325° C. in a pressurized reactor zone to convert olefins to heavier hydrocarbons.

2. The process of claim 1 comprising the further steps of reducing pressure on effluent from the reactor zone to flash volatile components into a vapor phase and recover a heavy liquid stream from a phase separator;

condensing a major portion of the vapor phase by cooling under pressure to recover a liquid intermediate olefinic stream and to recover condensed water by-product from oxygenate conversion to hydrocarbons; and fractionating the heavy liquid stream from the flashed reactor effluent to recover a distillate hydrocarbon product stream; and combining olefinic feedstock with a pressurized liquid diluent stream comprising a major fraction of the intermediate olefinic stream.

3. The process of claim 1 wherein the hydrogen is co-fed with feedstock in an amount sufficient to inhibit coke formation, and the catalyst comprises acid aluminosilicate zeolite having a constraint index of about 1 to 12 and a silica to alumina mole ratio of at least 12.

4. The process of claim 1 wherein the acid zeolite catalyst comprises a ZSM-5 type zeolite and is essentially free of hydrogenation components.

5. The process of claim 2 wherein the feedstock is combined with the olefinic recycle stream in a ratio of at least about 2 moles of recycle per mole of feedstock olefin and contacted with a fixed bed of acid aluminosilicate zeolite catalyst having a constraint index of about 1 to 12 at a reaction temperature of about 230° C. to 325° C. at process pressure of about 4000 to 7000 kPa to convert a major amount of feedstock olefins.

6. A process for converting synthol olefinic liquid product of Fischer-Tropsch synthesis to distillate hydrocarbons comprising the steps of contacting said synthol product at temperature of about 230° C. to 325° C. under pressure with acid zeolite conversion catalyst to oligomerize olefins and convert oxygenated hydrocarbons contained in said synthol liquid product, thereby providing an effluent containing heavy distillate range hydrocarbon, light gas and byproduct water;

co-feeding with said synthol product an amount of hydrogen gas in the range of about 1 to 50 mole percent and sufficient to inhibit coke formation during conversion; and separating said effluent to recover a heavy distillate-rich product stream, light hydrocarbon-rich vapor containing hydrogen and byproduct water.

7. The process of claim 6 wherein the distillate-rich liquid stream is fractionated to provide a major product stream consisting essentially of 154° C.+ aliphatic hydrocarbons comprising a major amount of $C_{10}$–$C_{20}$ aliphatic hydrocarbons.

8. The process of claim 7 wherein the hydrogen is mixed with the synthol product in an amount substantially proportionate to the oxygenated organic compound content thereof.

9. The process of claim 6 wherein the catalyst consists essentially of HZSM-5 zeolite.

10. The process of claim 9 wherein the acid zeolite has an acid cracking value ($\alpha$) of at least 120 and is essentially free of metal hydrogenation components.

11. A continuous process for converting a feedstock mixture comprising a major amount of $C_3$–$C_6$ olefins and a minor amount of oxygenated hydrocarbons to higher hydrocarbons including $C_{10}$–$C_{20}$ distillate product comprising:

contacting the feedstock in the presence of hydrogen with a shape selective acidic pentasil zeolite oligomerization catalyst under reaction conditions at a temperature of about 230° C. to 325° C. in a pressurized reactor zone to convert olefins to heavier hydrocarbons, wherein the hydrogen is co-fed in an amount comprising about 1 to 50 mole perecent of the feedstock.

12. The process of claim 11 wherein the acid zeolite catalyst comprises a ZSM-5 type zeolite and is essentially free of hydrogenation components.

13. The process of claim 11 wherein the feedstock is combined with an olefinic recycle stream and contacted with a fixed bed of acid aluminosilicate zeolite catalyst having a constraint index of about 1 to 12 at process pressure up to about 800 psig and hydrogen partial pressure up to about 50 psi to convert a major amount of feedstock olefins.

* * * * *